Figure 1:
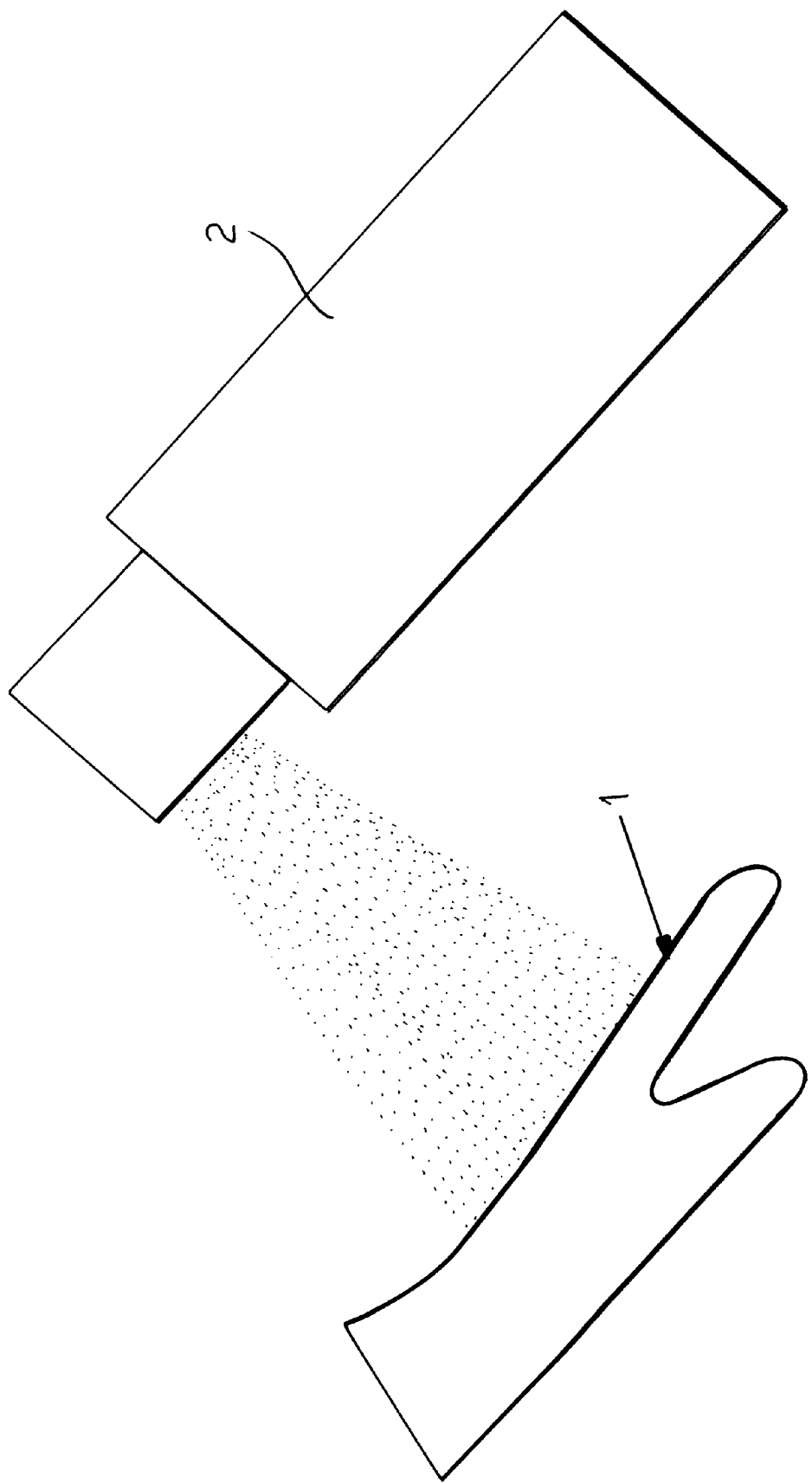

United States Patent [19]
Vetter

[11] Patent Number: 6,027,492
[45] Date of Patent: *Feb. 22, 2000

[54] METHOD FOR PROVIDING ACCESS TO A VEIN AS WELL AS DEVICE FOR PERFORMING THE METHOD

[75] Inventor: Helmut Vetter, Ravensburg, Germany

[73] Assignee: Arzneimittel GmbH Apotheker Vetter & Ravensburg, Ravensburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/583,088

[22] PCT Filed: May 8, 1995

[86] PCT No.: PCT/DE95/00628

§ 371 Date: Jan. 11, 1996

§ 102(e) Date: Jan. 11, 1996

[87] PCT Pub. No.: WO95/31242

PCT Pub. Date: Nov. 23, 1995

[30] Foreign Application Priority Data

May 11, 1994 [DE] Germany .............................. 44 16 656

[51] Int. Cl.[7] .................................................. A61M 5/00
[52] U.S. Cl. .................................. 606/2; 606/10; 606/13; 604/21; 600/310; 600/474; 600/477; 600/500
[58] Field of Search ................. 606/2–19; 128/630–634; 604/21; 600/310, 473–478, 500

[56] References Cited

U.S. PATENT DOCUMENTS

| | | | |
|---|---|---|---|
| 4,913,142 | 4/1990 | Kittrell et al. | 606/7 |
| 4,929,246 | 5/1990 | Sinofsky | 606/8 |
| 5,165,418 | 11/1992 | Tankovich | 606/16 |
| 5,275,596 | 1/1994 | Long et al. | |
| 5,522,813 | 6/1996 | Trelles | 606/2 |

FOREIGN PATENT DOCUMENTS

| | | | |
|---|---|---|---|
| 0 111 060 | 6/1984 | European Pat. Off. | |
| 0 464 207 A1 | 1/1992 | European Pat. Off. | |
| 31 29 931 C2 | 10/1983 | Germany | |
| 31 40 192 C2 | 5/1985 | Germany | |
| 91 90 181 | 9/1993 | Germany | |
| 8601728 | 3/1986 | WIPO | 128/634 |
| WO 94/06510 | 3/1994 | WIPO | |

*Primary Examiner*—David M. Shay
*Attorney, Agent, or Firm*—Herbert Dubno

[57] ABSTRACT

The invention relates to a method for creating a vein access, particularly on the human body, wherein at first the area of the skin surface (1) surrounding the vein access is disinfected, than the epiderm (3) is penetrated and the vein (4) opened and wherein finally a cannula part (5) is inserted in the vein (4). Further the invention relates to a device for implementing the method. Thereby the penetration of the epiderm (3) and/or the opening of the vein (4) are performed by a cutting device (6) operating with electromagnetic radiation.

21 Claims, 15 Drawing Sheets

Figure 13D:
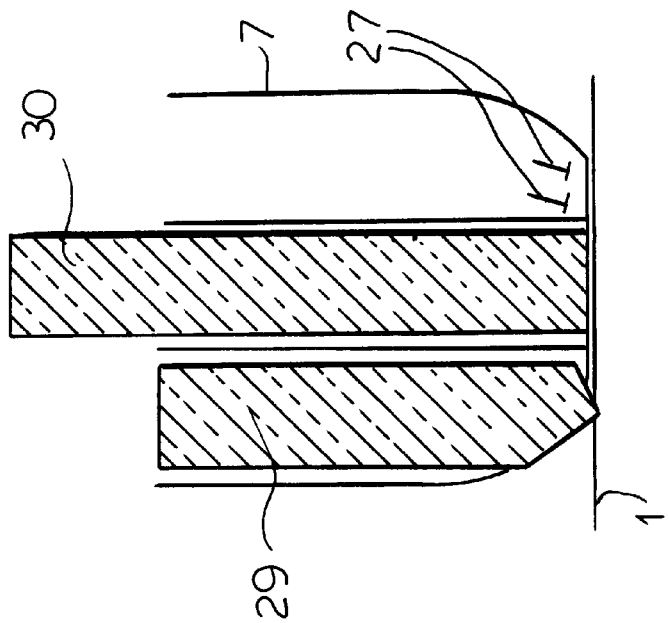

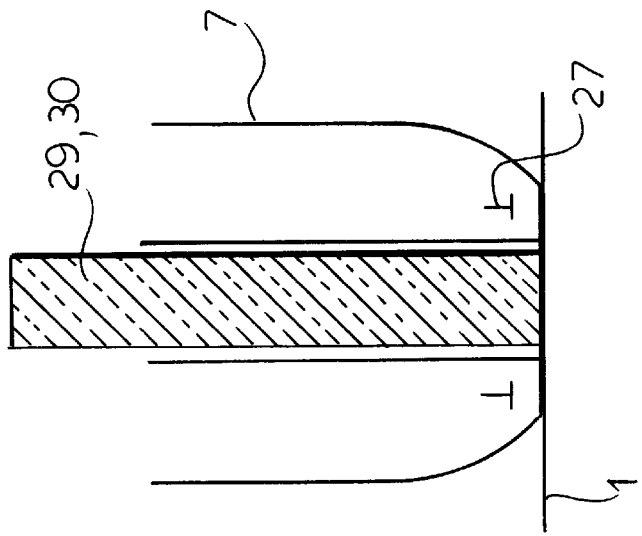
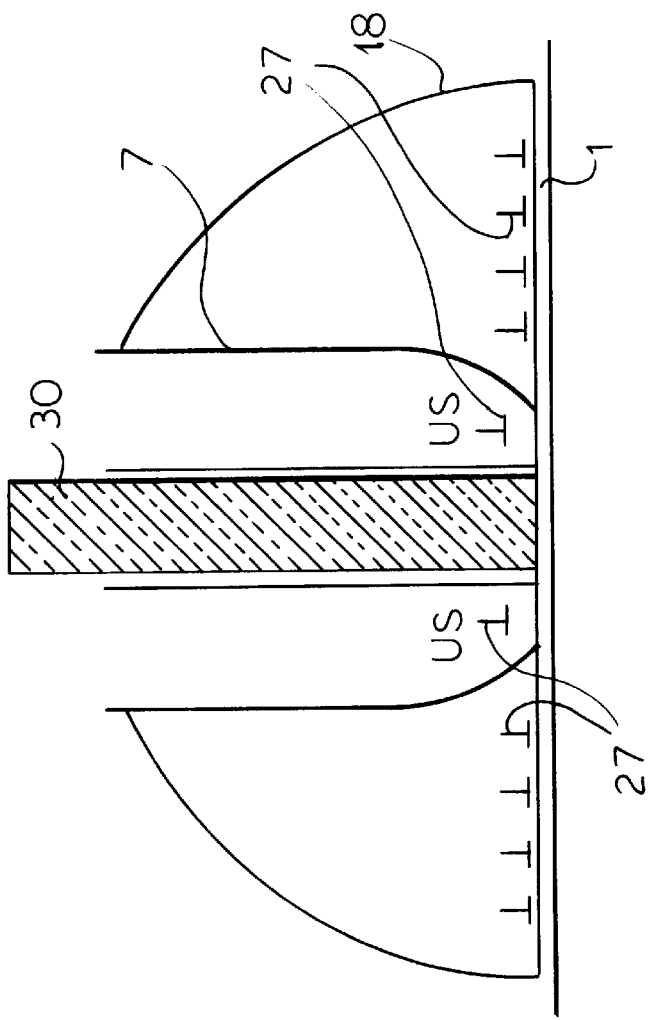
FIG.13b
FIG.13a

METHOD FOR PROVIDING ACCESS TO A VEIN AS WELL AS DEVICE FOR PERFORMING THE METHOD

The invention relates to a method of creating access to a vein, especially on the human body, whereby at first the skin surface surrounding the vein access area is disinfected, than the epiderm is penetrated and the vein is opened, and finally a part of a cannula is inserted. Further the invention relates to a device for implementing the method.

In order to provide a vein access which is supposed to be used over a longer period of time, usually cannulae of plastic material with a blunt end are used. In order to be able to introduce these—relatively soft—plastic cannulae into the vein common metallic cannulae are used which are inserted into the cannula of plastic material and extend beyond the plastic cannula with their slanted ends. As soon as the plastic cannula is in the desired position inside the vein, the metallic cannula is withdrawn.

The penetration of the epiderm and the opening of the vein by purely mechanical ways can have a negative influence on the provided vein access, so that for instance the latter has to be removed sooner than anticipated, due to occurring infections. This can also have a negative influence on the healing process starting after the removal of the vein access.

It is the object of the invention to improve the method mentioned in the introduction from the medical point of view, and furthermore to make it more agreeable to the patient. Further it is the object of the invention to create a device for implementing this method.

From the method point of view this object is achieved due to the fact that the penetration of the epidermis and/or the opening of the vein is performed with a cutting device working with electromagnetic radiation.

The advantage afforded by the invention consists basically in that the application of electromagnetic radiation already advantageously used in other medical fields, makes possible the cutting of tissues with favorable results and in addition has a positive influence on the subsequent healing.

In a preferred embodiment of the method the wave length of the electromagnetic radiation lies within the range of visible light, respectively within neighboring ranges.

Further the invention provides that the cutting device be at first adjusted by a measuring mechanism selectively reacting to blood vessels and fastened and in its adjusted position fastened to the skin surface. This insures that the vein is reached without the frequent failed attempts which can be seen with the current techniques.

Thereby within the framework of the invention it can be further provided that prior to the use of the cutting device, a locally acting anaesthetic be applied in the area where the epiderm is supposed to be penetrated. A particularly simple handling results when the application of the anaesthetic takes place together with the fastening of the cutting device on the skin surface.

From the device point of view the object of the invention is achieved starting out from a contact piece to be fastened to the skin surface, which has one or more attachment pieces for the connection of syringes, infusion tubes or the like, as well as cannula part through which an access particularly to a vein is created, due to the fact that the contact piece is equipped with a cutting device working with electromagnetic radiation.

This cutting device suitably works with light of high energy in the visible or neighboring ranges. Thereby it has further to be considered advantageous when the cutting device works with monochromatic light.

In a preferred embodiment of the invention the cutting device is formed by a light-conducting element to which a light source is connected. Thereby the light-conducting element can suitably consist of a sleeve which surrounds the cannula part. The sleeve can thereby have one or more optical guide rods.

In a first and very advantageous embodiment of the invention the sleeve part has two optical guide rods, which area diametrically opposed to each other. As a result a linear section can be performed between the two conducting rods.

Also there is the similarly suitable possibility to design the entire sleeve part as an optical guide rod. In order to make possible the coupling of the light in a simple way, the invention provides that one end of the optical guide rod, respectively rods, abuts respectively abut in one of the attachment pieces. This way the further possibility exists that the connection of the optical guide rod, respectively rods, with the light source be made through a connection line equipped with optical fibers which can be connected to the attachment piece.

In order to be able to introduce in a simple manner the cannula part after the opening of the vein, the cannula part is arranged longitudinally slidable in the sleeve part. For the purpose of simpler handling in the connection line at the side which is to be connected to the attachment, a setting element for the axial displacement of the cannula part is provided. Due to this the cannula part can be inserted into the vein immediately after the opening of the vein, when the connection line is still in the attachment piece.

In order to give the device a sufficient hold, the contact piece is provided with an adhesive foil for fastening to the skin surface. Further for a better connection between the contact piece and the adhesive foil, a connection part in the shape of a spherical segment is provided, wherein the contact piece is embedded with its end creating the vein access, whereby the adhesive foil is applied against the flat surface of the spherical segment. It has further proven to be advantageous when the adhesive foil has a cushion soaked in anaesthetic in the area of the end creating the vein access. Then it is further advisable that the adhesive foil be provided with a detachable protective foil on the side which comes to lie on the skin surface.

According to an advantageous further development of the invention a measuring device is provided for the adjustment of the cutting device to the vein to be accessed. This measuring device advantageously has a measuring light source and a detector selectively receiving the measuring signal transmitted or reflected by the skin surface. Within the framework of the invention, the output signal of the detector is fed to an analog, digital evaluation unit, or to one working with fuzzy logic. In order to simplify the mounting of the contact part, the evaluation unit can have an optic and/or acoustic signal emitter indicating the orientation of the cutting device with respect to the vein to be accessed.

Further for the transmission to the detector of the measuring signal transmitted or reflected by the skin surface a photoconductor extending through the cannula part is advantageously provided. Thereby in a particularly simple design the photoconductor can be provided for the transmission of the measuring light as well as of the transmitted, respectively reflected measuring signal to the detector and for this purpose be guided over an optical beam separator, through which the measuring light is directed into the photoconductor and the measuring signal to be fed to the detector is released.

The light source for the cutting device is advantageously composed of a laser of appropriate wave length. It is also possible to provide a laser of appropriate wave length as a source of measuring light. Thereby exists also the possibility that the light source for the cutting device and the measuring light source consist of a common laser whose output and/or wave length can be adjusted.

Finally there is also the possibility that the measuring device comprises an ultrasound emitter and an ultrasound receiver for determining the position and the depth of the vessel to be punctured. Thereby all ultrasound measuring methods known to medical techniques can be used, through which the position of the vessel to be punctured can be made visible, respectively recognizable to possibly automatically operating control devices.

Figure 2:
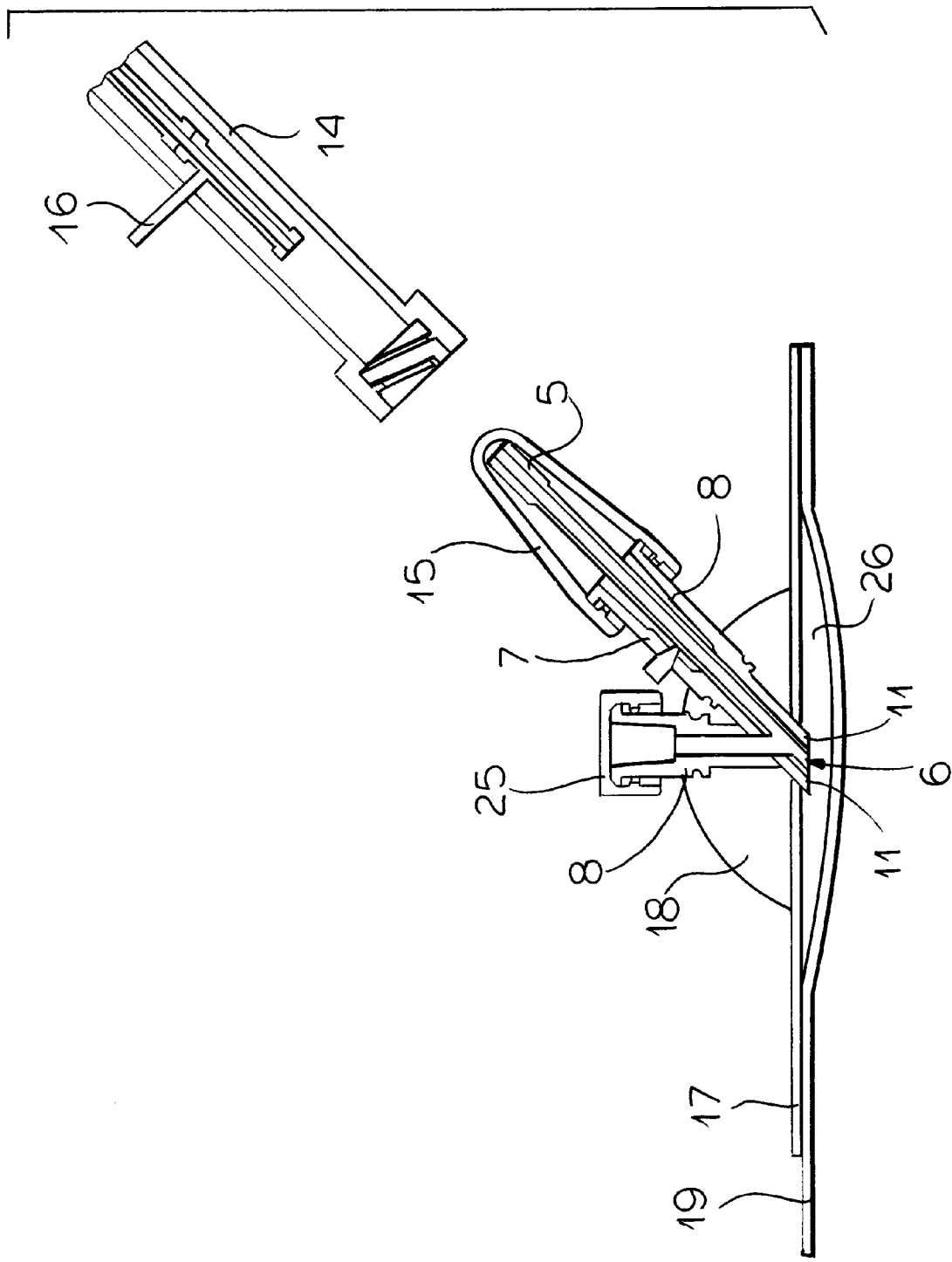
Figure 3:
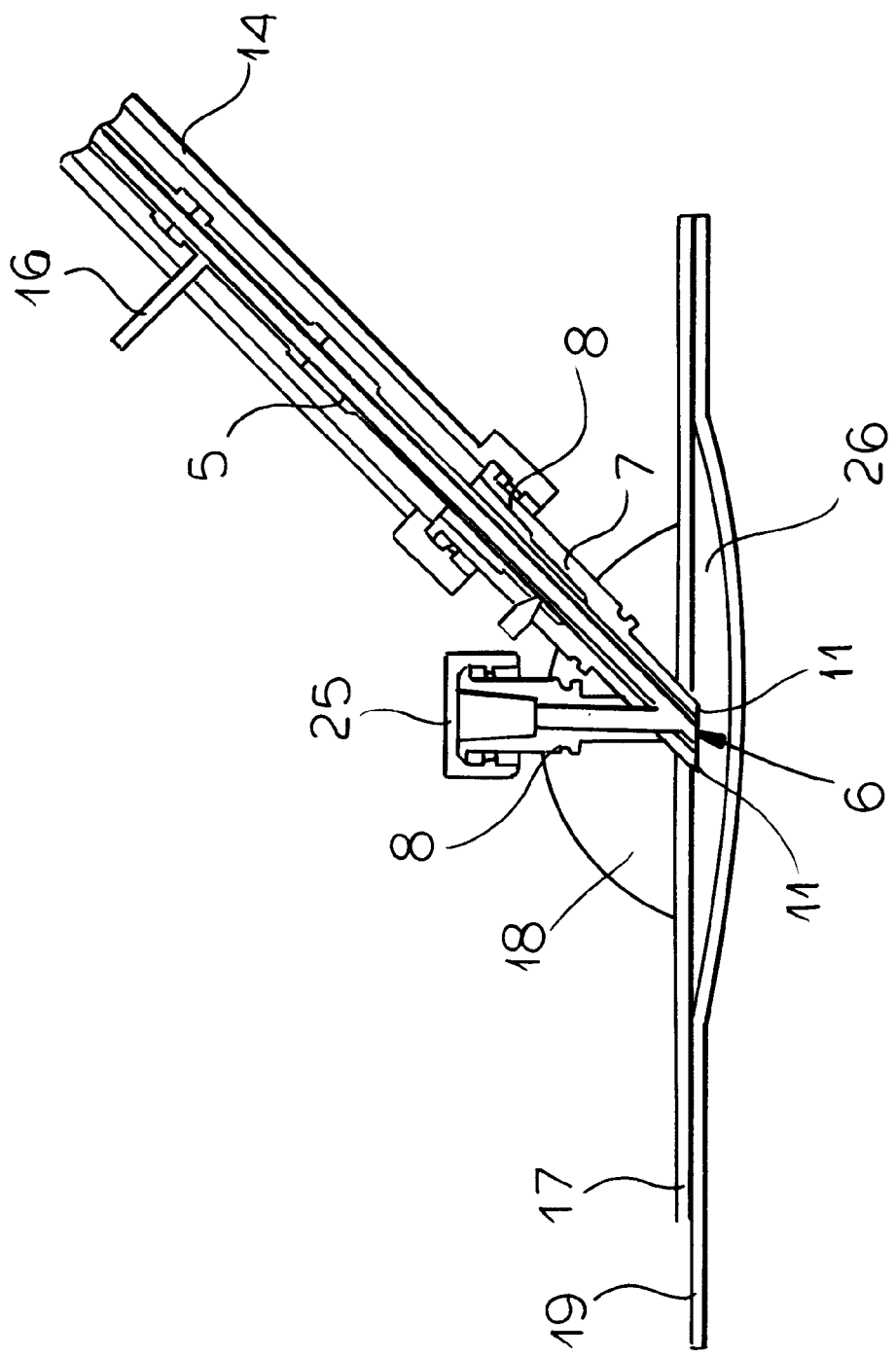
Figure 4:
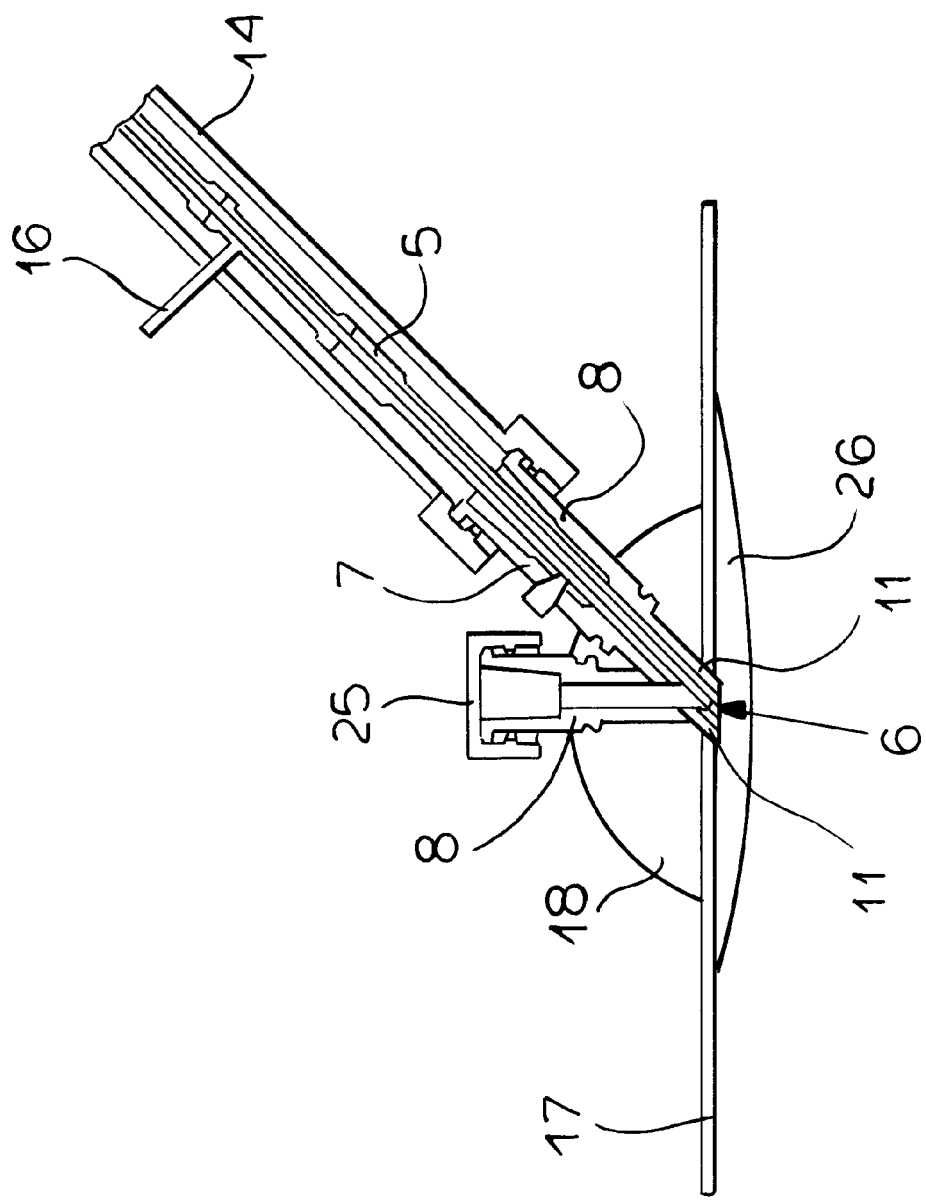
Figure 5:
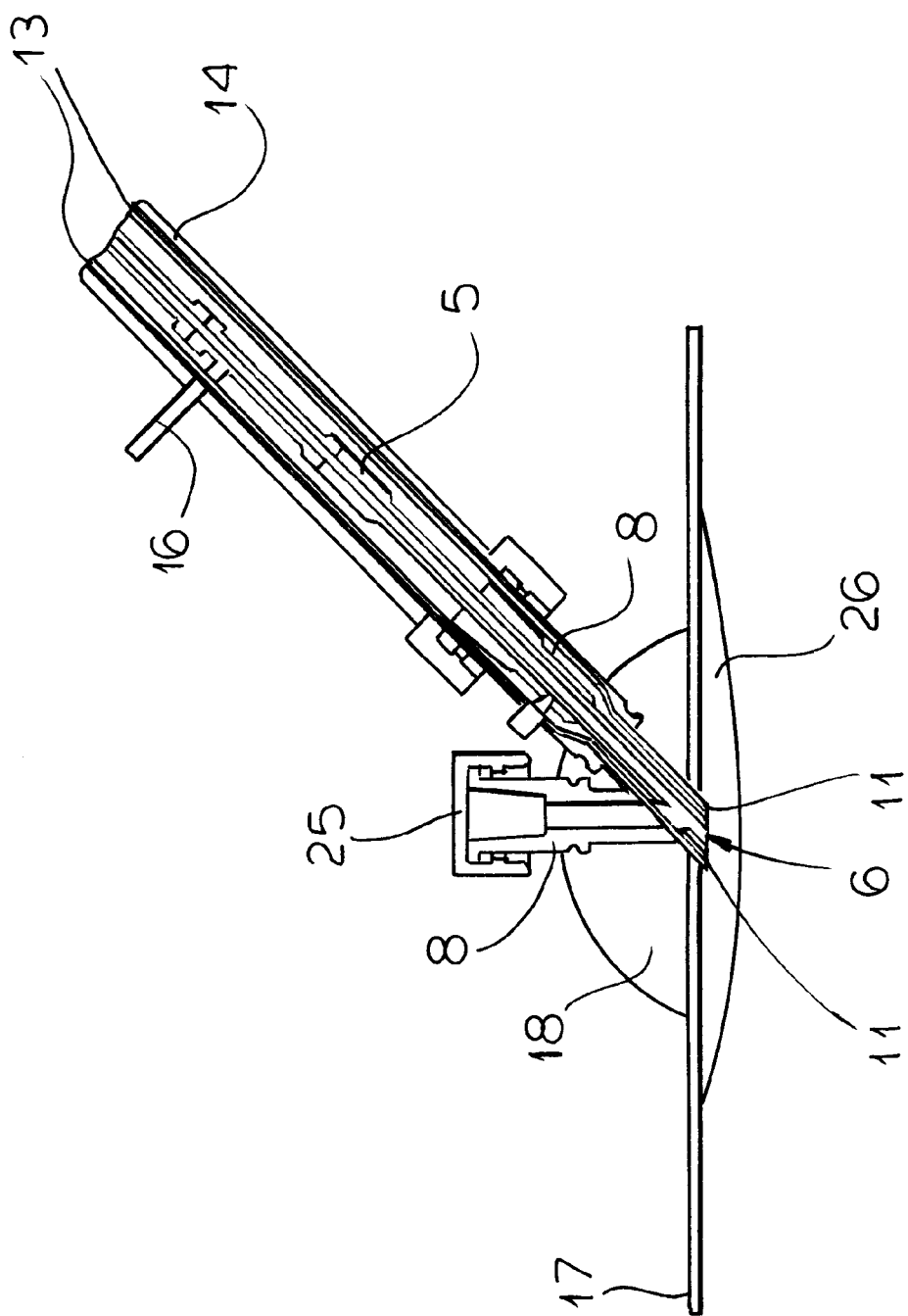
Figure 6:
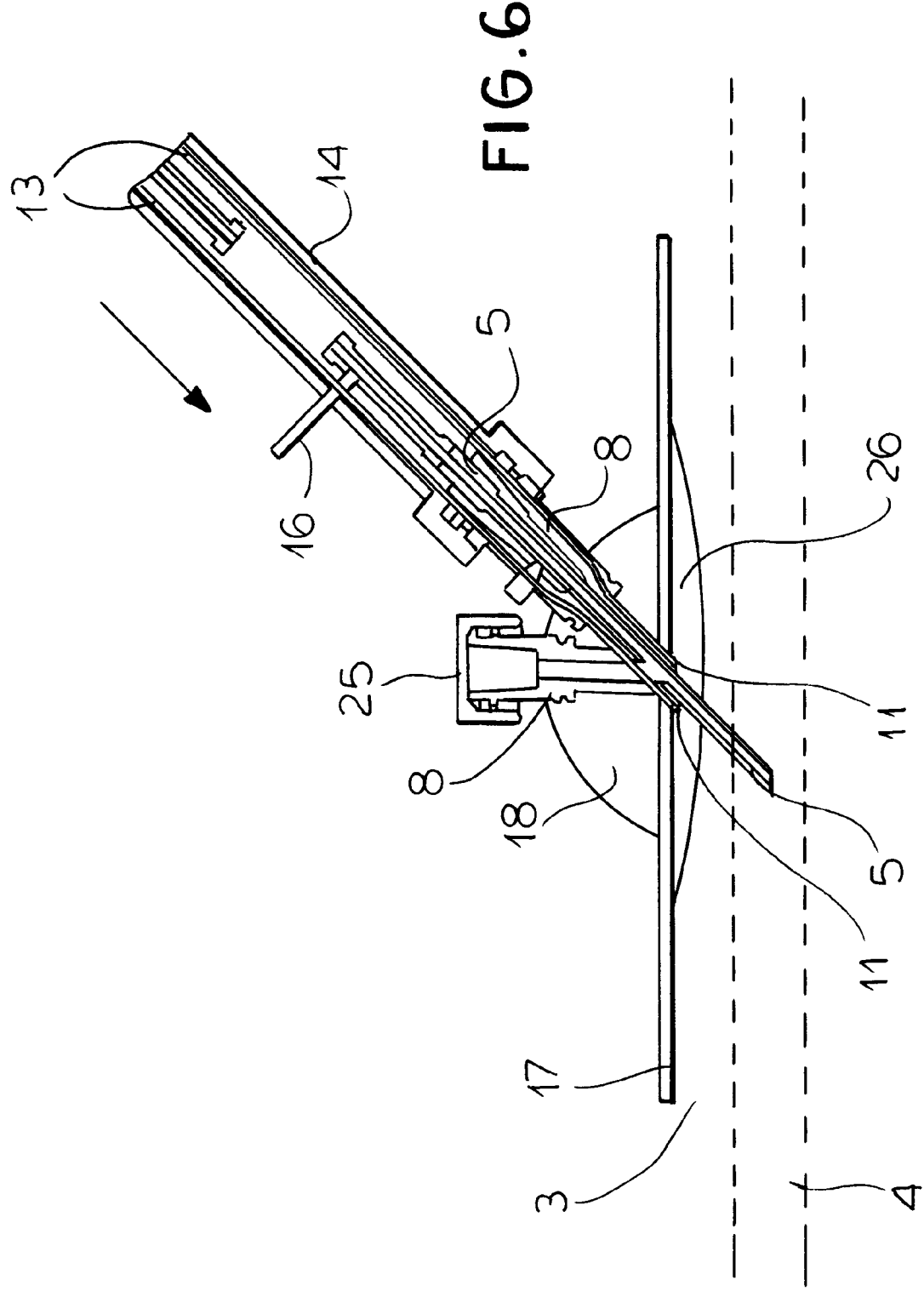
Figure 7:
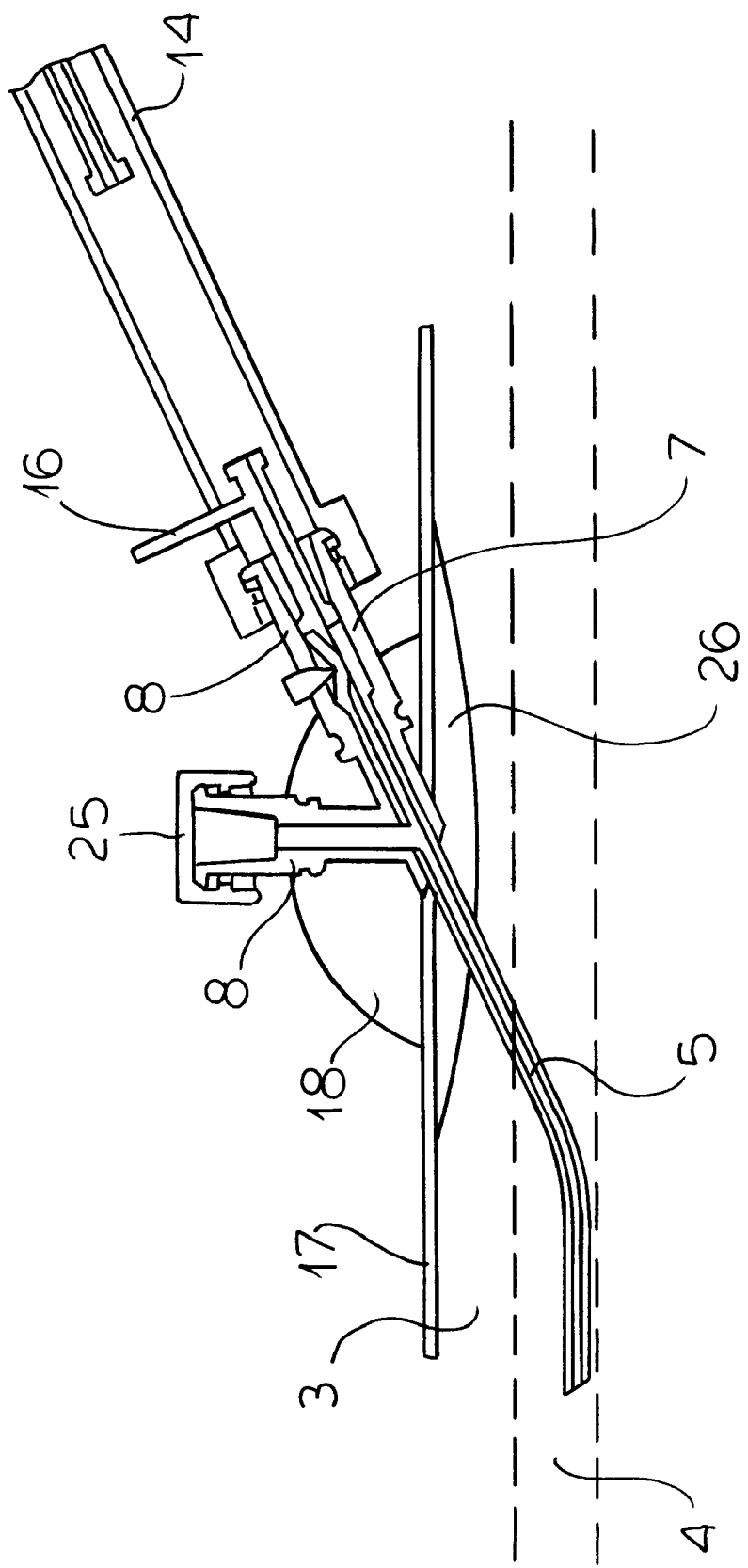
Figure 8:
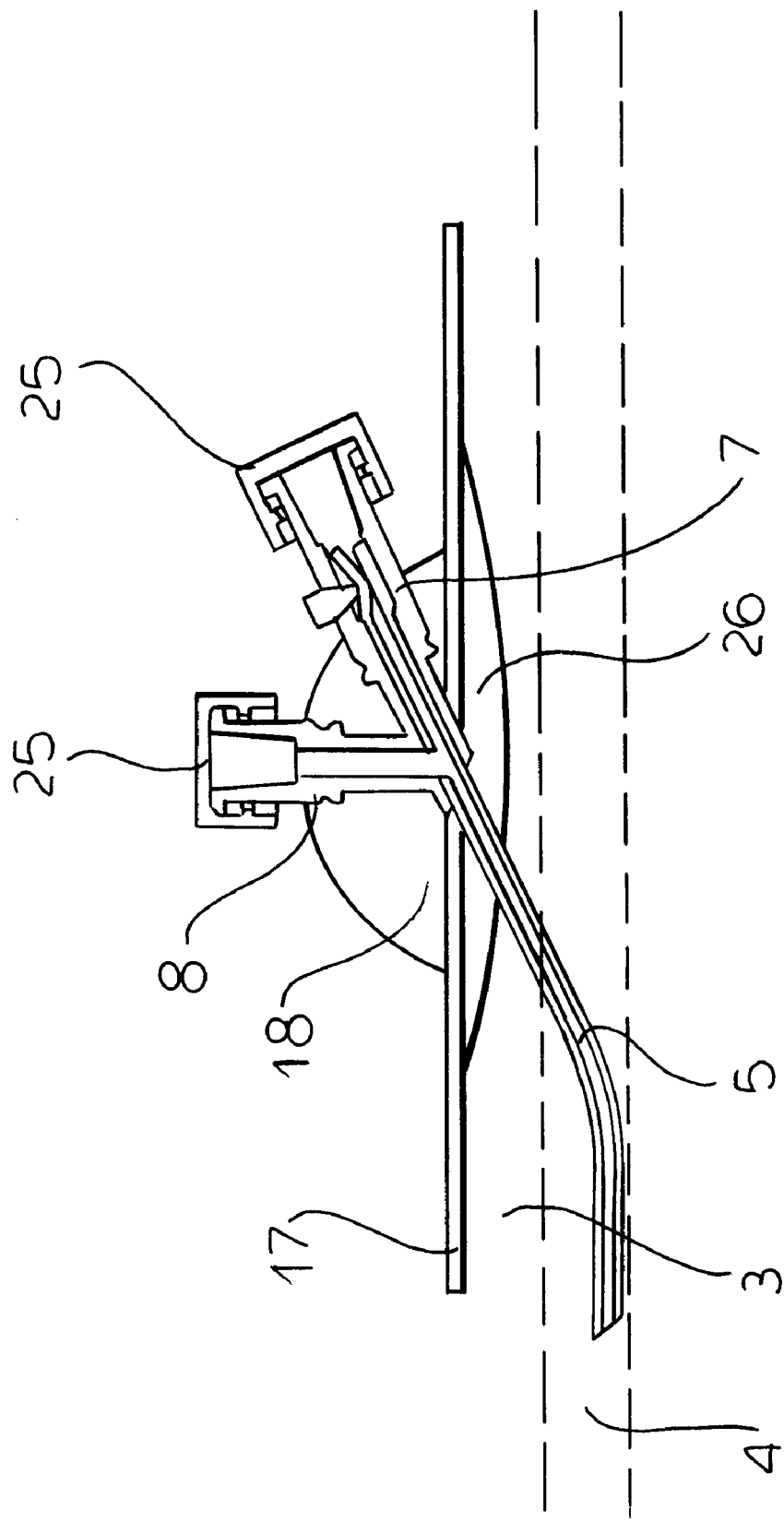
Figure 9:
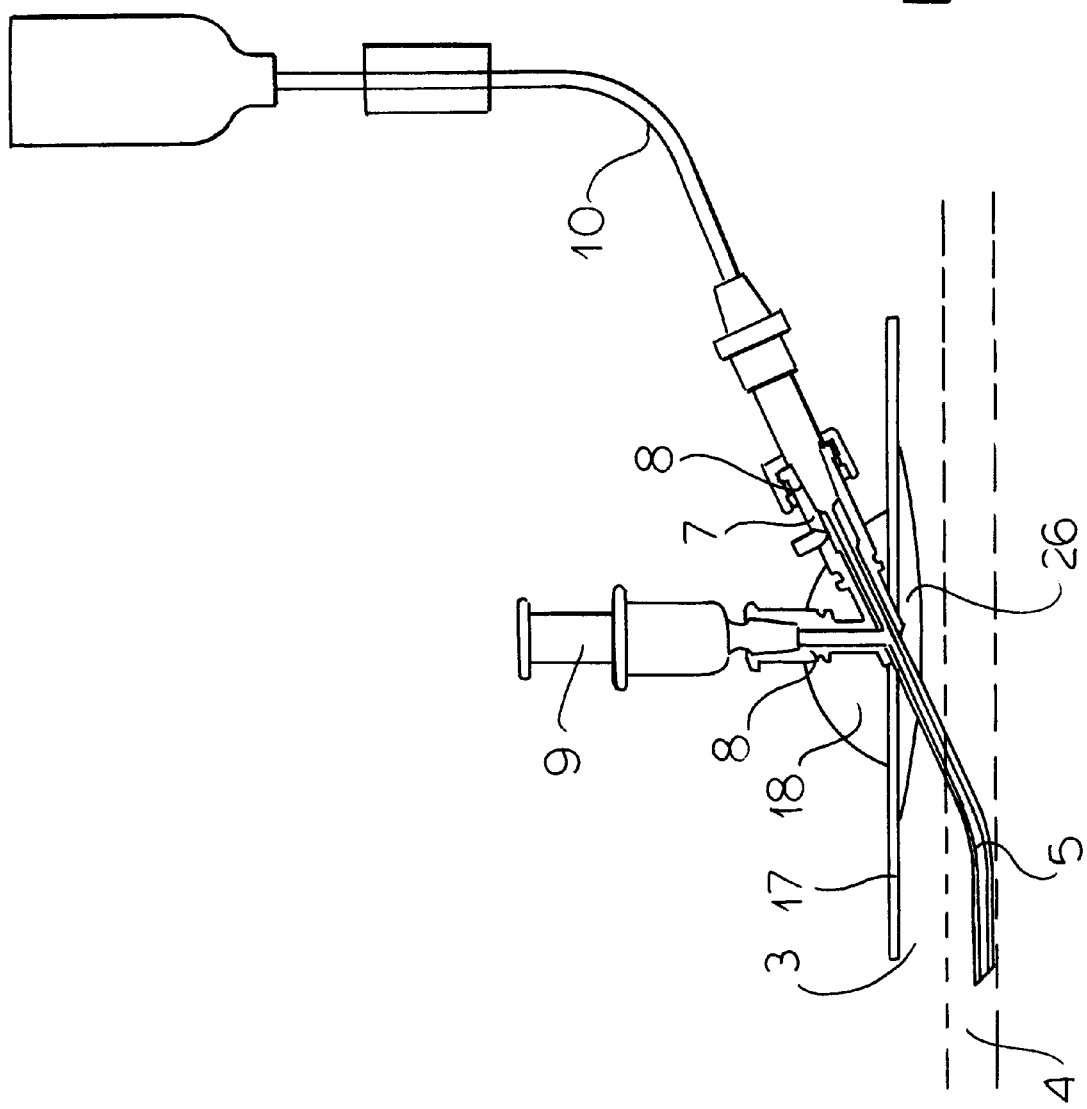
Figure 10:
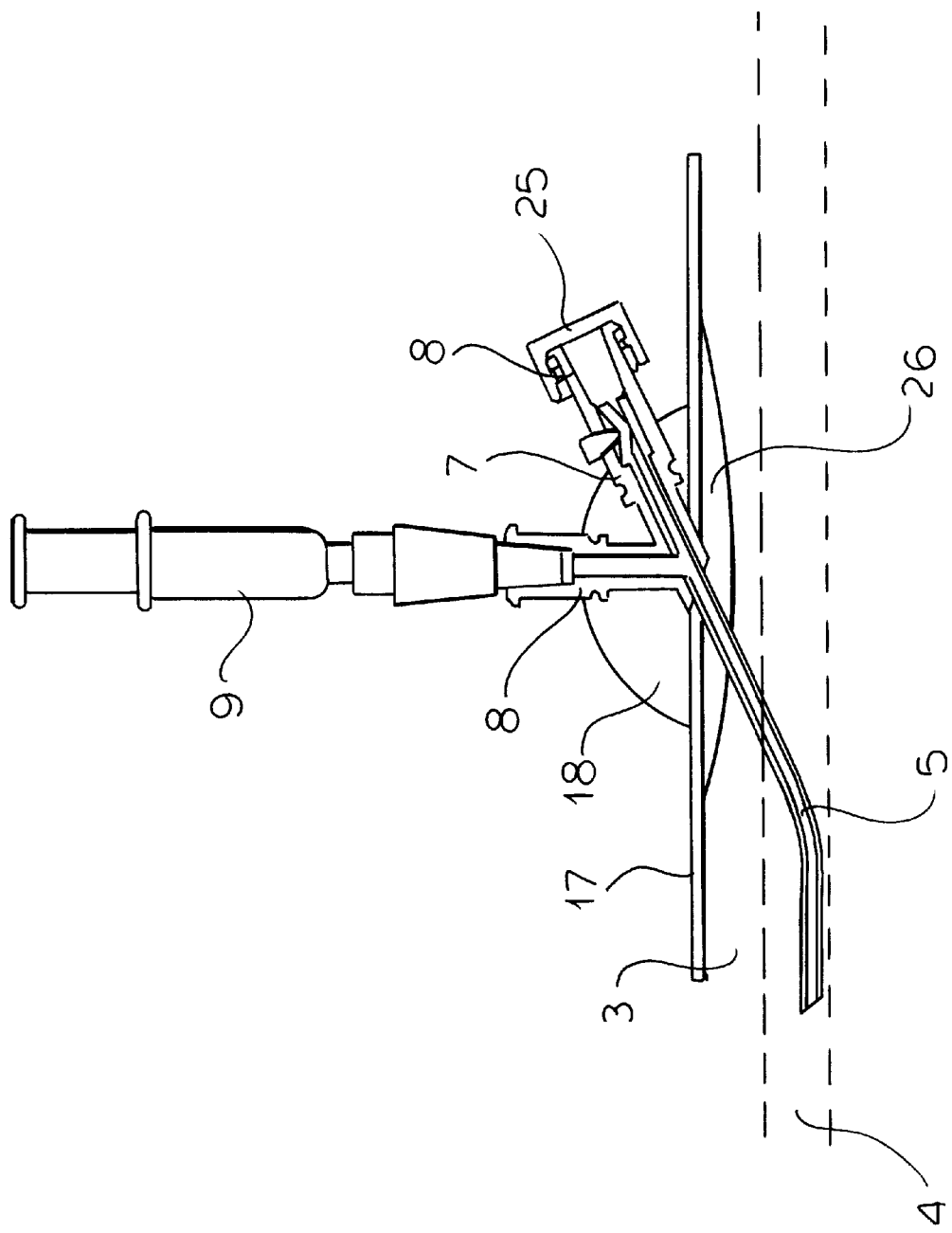
Figure 11:
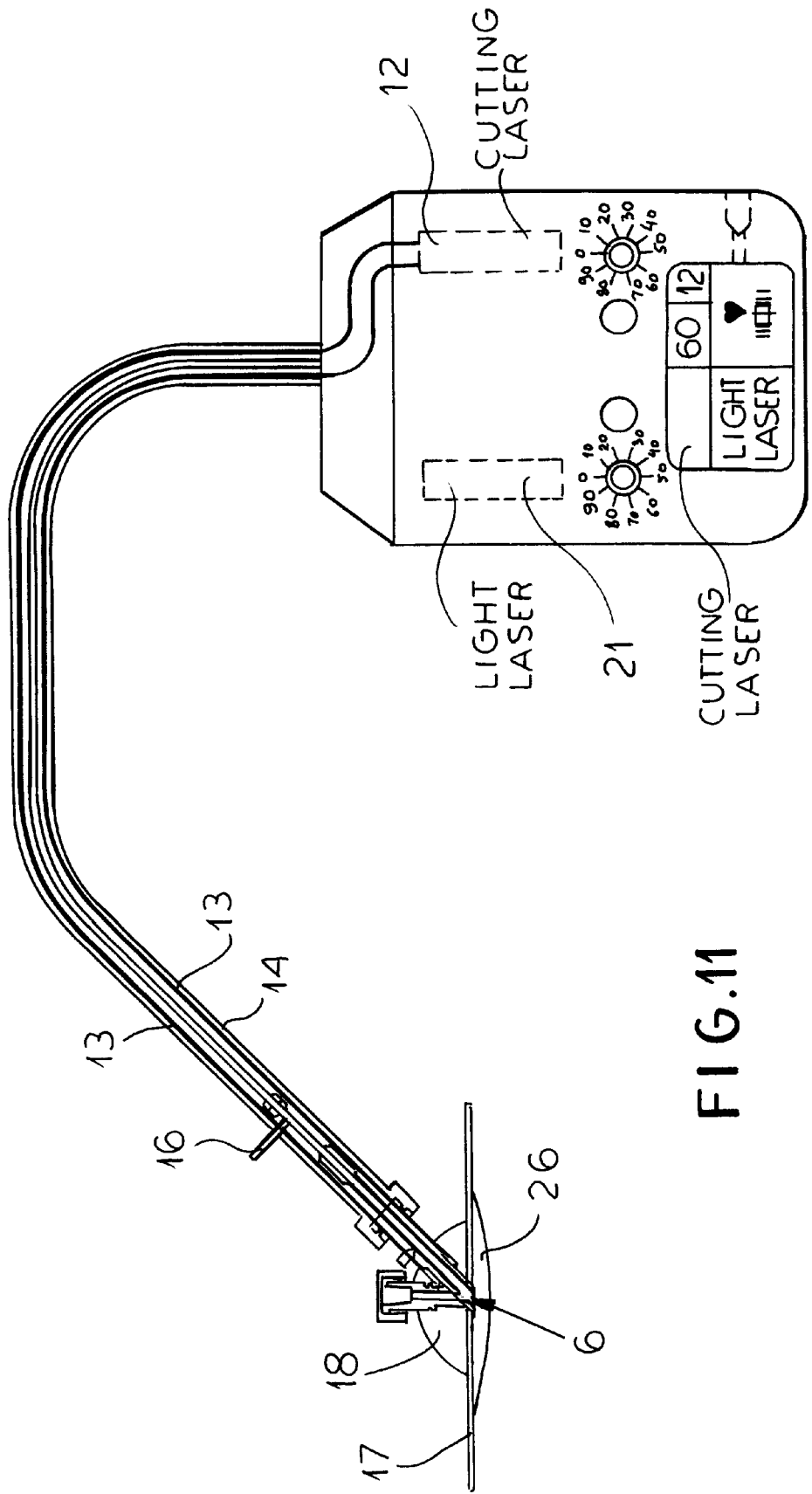
Figure 12:
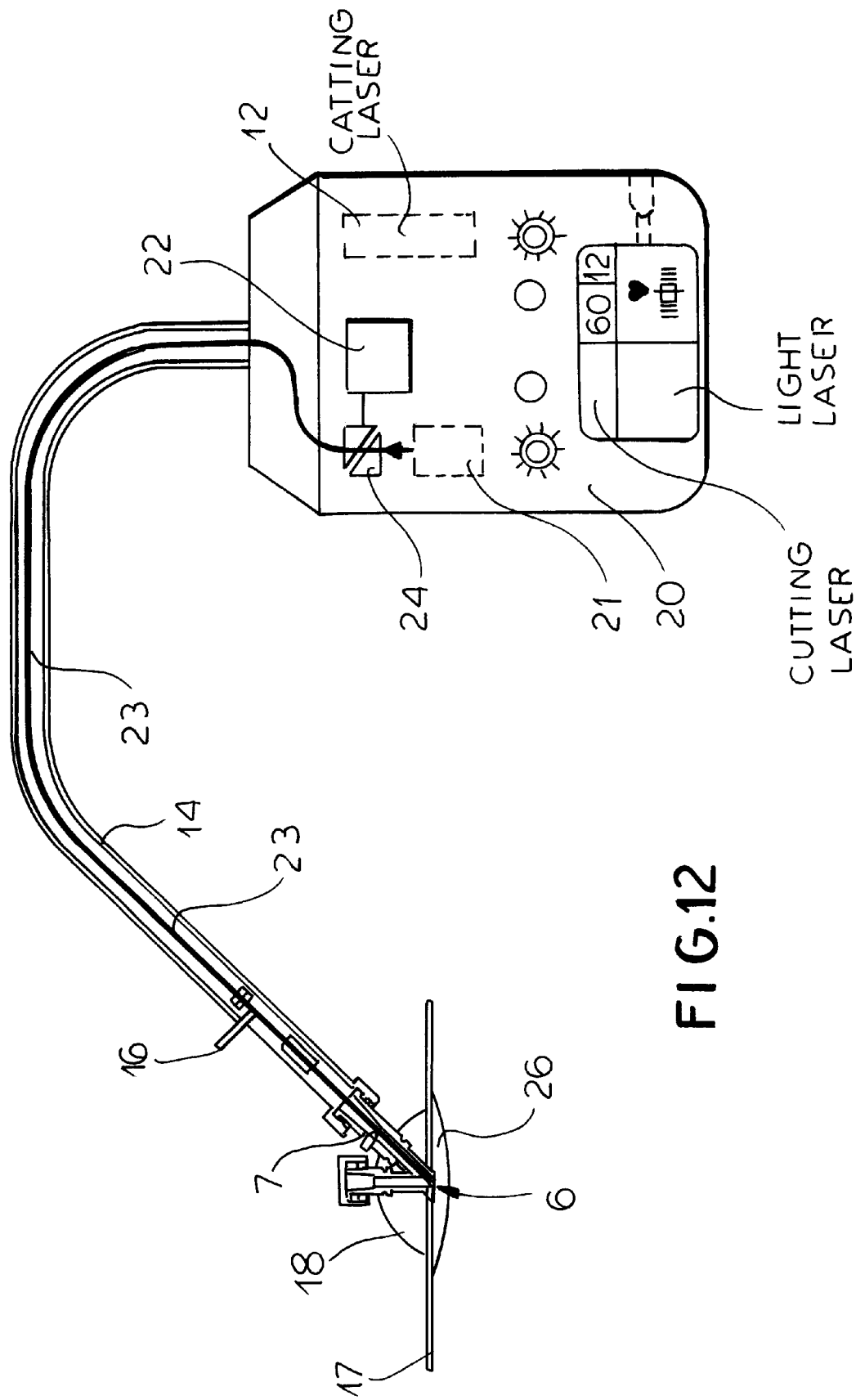
Figure 13C:
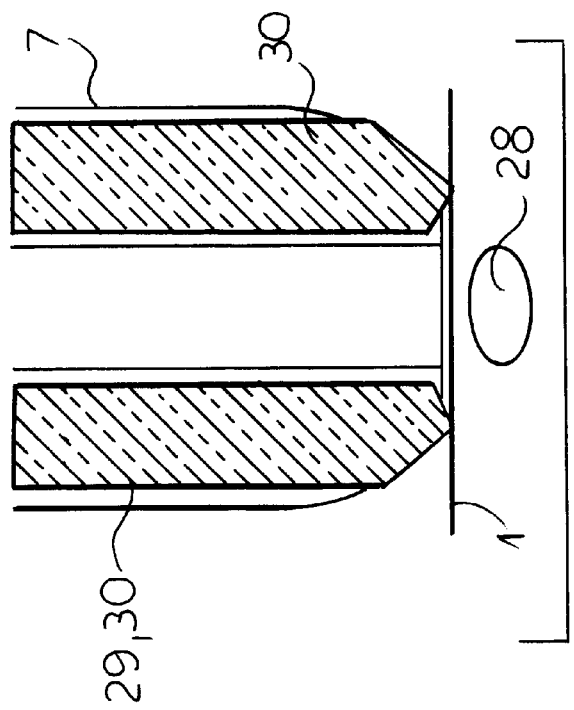
Figure 14:
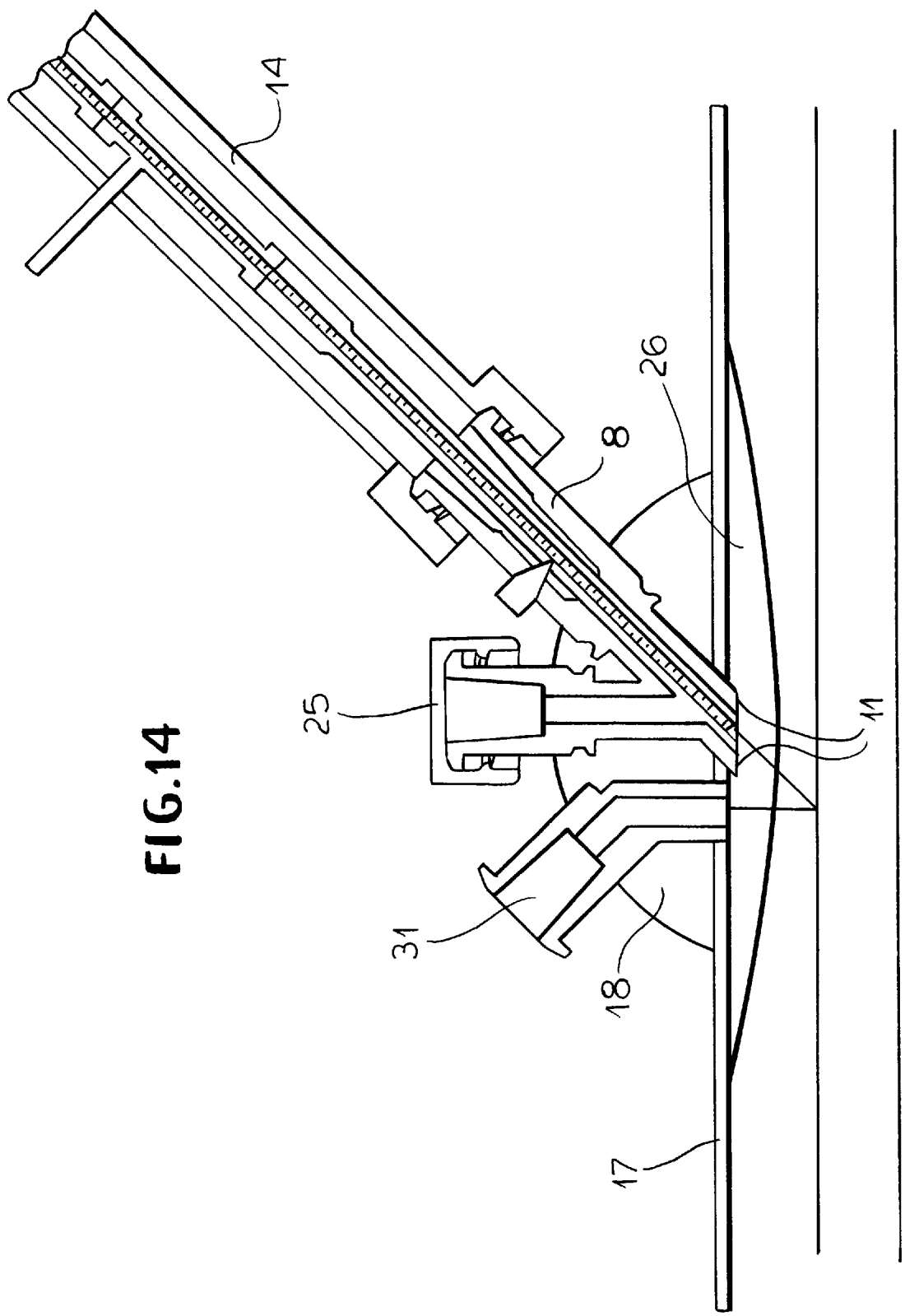

In the following the invention is closer described with the aid of the embodiment examples represented in the drawing; it shows:

FIG. 1 the application of disinfectant prior to creating the vein access,

FIG. 2 the contact part of the device to be affixed to the skin surface,

FIG. 3 the object according to FIG. 2, but with attached connection line,

FIG. 4 the object according to FIG. 3 but with inserted photo-conductive fibers for a measuring device, FIG. 5 the contact part at the moment of vein opening, FIG. 6 the contact part at the moment when the cannula is inserted, FIG. 7 the contact part at the moment when the cannula is completely inserted, FIG. 8 the contact part with closed attachment pieces, FIG. 9 the contact part with connected infusion and syringe, FIG. 10 the contact part with connected syringe for blood extraction, FIGS. 11 and 12 schematic representations of two embodiments of the entire device, FIG. 13 partial sections a) to d) showing various possibilities of use in creating the vein access, FIG. 14 the object according to FIG. 4, but with an additional adapter for an external ultrasound device or a laser.

The device shown in the drawing serves for creating an access to a vein, particularly on the human body, whereby at first the according to FIG. 1 the skin surface 1 surrounding the vein access is disinfected, for instance with a spray can 2. Subsequently, according to common practice the epiderm 3 is penetrated by a cannula and the vein 4 is opened, whereby at the same time—an elastic—cannula part 5 is inserted into the vein 4. Since such vein accesses are provided not only for short term, but also for a longer period of time, the penetration of the epiderm 3 as well as the opening of vein 4 have to be done in the most protective manner.

This is done specifically by means of a cutting device operating with electromagnetic radiation. This cutting device 6 is provided on a contact piece 7 which is to be fastened to the skin surface 1, which has one or more attachment pieces for the connection of syringes 9, infusion tubes 10 or the like. Further the contact piece 7 is provided with the cannula part 5, through which the access to the vein 4 is created.

The cutting device 6 works with light of high energy in the visible or the thereto neighboring ranges, whereby it is particularly advantageous when the cutting device 6 works with monochromatic light.

The cutting device 6 itself consists of a photoconductive element 11, to which a corresponding light source 12 is connected. In the embodiment example the photoconductive element 11 is formed by a sleeve part surrounding the cannula part 5. This sleeve part can have one or more optical guide rods in a manner which is not closer shown in the drawing. If the sleeve part is equipped with two optical guide rods, then there are suitably located diametrically opposite to each other, in order to create a corresponding cutting line. However there is also the possibility indicated in FIG. 5 wherein the entire sleeve part is built like an optical guide rod. In this case a circular, or in the case of an inclined position of the attachment piece 8 such as indicated in the embodiment example, an oval section shape results on the skin surface 1.

The one end of the optical guide rod, respectively rods, facing away from the skin surface 1 abuts in one of the attachment pieces 8. Then the connection between the optical guide rod, respectively rods, and the light source 12 can take place through a connection line 14 provided with optical fibers 13 and which can be attached to the attachment piece 8, as can be seen from instance from FIG. 4 to 6. The optical fibers 13 are coupled in the attachment piece 8 to the optical guide rods, respectively the sleeve part. The cannula part 5, which in FIG. 2 is in its retracted position and is protected by a closing cap 15 set onto the attachment piece 8, is arranged longitudinally slidable in the sleeve part, so that after the opening of the vein 4 it can be inserted therein according to the illustration of FIG. 6. For this purpose in the connection line 14 on the side to be connected to the attachment piece 8 a setting element 16 is further provided, which makes possible the axial displacement of the cannula part from the outside.

In order to be able to safely fasten the contact part 7 to the skin surface 1 the former is provided with an adhesive foil 17. The connection between the contact part 7 and the adhesive foil 17 takes place via a connection piece 18, having the shape of a spherical section. The contact piece 7 is embedded in this connection piece 18 with its end creating the vein access, while the adhesive foil 17 rests against the flat surface of the spherical section.

In the area of the end of the contact piece 7 creating the vein access, the adhesive foil 17 bears a cushion 26 soaked in a liquid anaesthetic. Therefore after the contact piece 7 is applied to the skin surface 1 the opening of the vein should not be performed before the anaesthetic had a chance to work. This way a vein access can be created in a totally painless way. According to the illustration in FIG. 2 the adhesive foil 17 is provided with a detachable protective foil 19 on the side which comes to be applied to the skin surface 1.

In order to correctly apply the contact part 7 to the skin surface 1, so that the vein can be accessed reliably and without failed attempts unpleasant to the patient, a measuring device 20 is provided, which makes possible an adjustment of the cutting device 6. For this purpose the measuring device 20 has a measuring light source 21 and a detector 22 selectively receiving the measuring signal transmitted or reflected by the skin surface. This measuring device 20 is based in principle on the so-called photoelectric plethysmography. The output signal of the detector 22 is then fed to an analog or digital evaluation unit, or an evaluation unit operating with fuzzy logic, which is not closer shown in the drawing. This evaluation unit can have an optical and/or an acoustical signal emitter, which indicates the resulted orientation of the cutting device 6 with respect to the vein 4 to be accessed.

However there is also the possibility not closer shown in the drawing to use as the measuring device 20 one or more ultrasound emitter and ultrasound receiver, which in a known manner are capable to deliver an image of the position of the vessel.

For the transmission of the measuring signal transmitted or reflected by the skin surface 1 to the detector 22 a photoconductor 23 is provided extending through the cannula part 5, as shown in FIG. 4 and 12. In order to transmit through this photoconductor 23 the measuring light as well as the transmitted, respectively reflected measuring signal to the detector 22, a beam separator 24 is provided, through which on the one hand the measuring light is directed into the photoconductor 23 and on the other hand the measuring signal to be fed to the detector 22 is put out.

As light source 12 for the cutting device 6 a laser of appropriate wave length is provided, which is merely indicated in the drawing. The measuring light source 21 can consist in a corresponding manner of a laser of appropriate wave length, however comparatively with a substantially lower output.

However there is also the possibility that the light source 12 for the cutting device 6 and the measuring light source 21 consist of a common laser with adjustable output and/or wave length. In that case the transmission of the light to the skin surface 1 can take place as shown in FIG. 11, while a central photoconductor 23 running through the connection line 14 according to FIG. 12 can be used for the transmission of the measuring signal to the detector 22. In this case the beam separator 24 illustrated in FIG. 12 could be dispensed with.

In order to open a vein access with the device of the invention, at first the skin surface is disinfected as shown in FIG. 1. Thereby the disinfectant can have a composition which causes the anaesthetic permeating the cushion 26 to dissolve quicker. After that according to FIG. 3 to the attachment piece 8 the connection line 14 is connected and a photoconductor 23 can be inserted in this line, as per FIG. 4. By means of the measuring device 20 an alignment of the contact piece, respectively of the cutting device 6 takes place, whereafter the adhesive foil 17 is pressed onto the skin surface 1, whereby the anaesthetic in the cushion 26 comes into contact with the skin surface 1. After the anaesthetic becomes effective, according to FIG. 5 the penetration of the epiderm 3 and the opening of vein 4 take place, so that subsequently according to FIG. 6 the cannula part 5 can be inserted in the opened vein 4 via the setting element 16.

After the cannula part 5 is completely inserted in the vein as in FIG. 7, the connection line 14 can be detached and the attachment piece 8 can be closed with a closing cap 25. As shown in FIGS. 9 and 10, according to need a syringe cylinder 9 or an infusion tube 10 can be connected in a manner known per se to the attachment piece 8.

In detail the following three ways to proceed result from the invention, which will be again described in a succinct manner:

When the connection piece 18 is applied a depth exploration of the vein to be punctured takes place at the same time, regarding its position and depth, whereby the thickness measurement of the tissue layers can be performed either by ultrasound or also by using laser light. In the latter case a (focussed) "orientation beam" such as the laser beam of the cutting laser is guided through the cannula part. The sensors collecting the reflecting beams are arranged, respectively integrated, close to the exit opening (cutting device 6) and/or in the connection piece 18 and/or in the contact piece 7. This is shown in detail in FIG. 13 in the partial sections a) to d). Subsequently the laser output required for cutting is set either manually or automatically with the aid of previously determined tissue parameters. The laser light is subsequently guided through the photoconductor, whereby a cutting channel with a suitable diameter is created, until the vessel to be reached is punctured. Subsequently the cannula part is guided through the created vein access (cutting channel) and introduced into the punctured vessel.

Instead of letting the photoconductor for the cutting laser run through the elastic cannula part, the light beam of the cutting laser can also be guided externally, e.g. through two optical fibers, whereby then the light beams exiting the optical fibers have then to be reunited in a focal point, so that the diameter of the focal point corresponds at least to the external diameter of the cannula part to be introduced. Thereby the (focussed) "orientation beam" is guided inside through the elastic cannula part. However it is also possible to guide the "orientation beam" externally, just like the light of the laser. The sensors collecting the reflected beams are again arranged close to the exit opening and/or integrated in the connection piece or in the attachment piece.

This first way to proceed is particularly suitable for vessels located close to the surface, when the danger of having the created vein access closed by neighboring tissue material, e.g. fatty tissues, prior, respectively during the introduction of the elastic cannula, is quite minimal.

In the second way to proceed again the application of the connection piece 18 is simultaneous with the exploration of the position and depth of the tissue layers by means of ultrasound or laser light. The adjustment of the laser output follows, whereby the focussed beam of the cutting laser is guided internally through a photoconductive element. The focal point of the focussed laser beam lies thereby directly before the opening of the cannula part to be inserted. By burning the cutting channel with the required diameter, the advancing cutting operation is followed by the cannula part guided through the cutting channel, corresponding to the penetrating depth of the cutting laser.

This way to proceed considerably minimizes the danger of having the vein access created by the cutting laser (cutting channel) closed by laterally adjacent tissue material before the insertion of the cannula, since the elastic cannula part follows the advancement of the cutting process. Therefore this procedure is particularly advantageous for deeper located vessels and also in persons with a relatively thick subcutaneous fatty tissue.

According to a third way to proceed the optic fiber element conducting the laser light is slidably received in the elastic cannula part and projects somewhat beyond the point of the cannula part. Thereby the optic fiber element is in direct contact with the tissue while the vein access is created. Thereby the optic fiber element can be separately withdrawn from the cannula part.

Here too the application of the contact piece coincides with the determination of the depths and location of the vessel, including the thickness measurement of the tissue layers by means of ultrasound or laser light. After setting the required beam output, while the vessel is being punctured the optic fiber element and the cannula part are displaced in a unit for the puncturing of the vessel wall. The displacement can be done manually or by means of a control unit (computer-controlled cannula guiding system). After the puncture was performed, the optic fiber element is withdrawn.

In this kind of procedure it can also be alternately provided that the photoconductive fiber be connected to the cannula part in such a manner that the laser light beam is further conducted in the elastic cannula part. Then the optic fiber element has no direct contact with the tissue.

The advantage of this contact method is that the position of the fiber point can be directly surveyed by means of an optic-fiber visualization device, also for instance through the method of magnetic resonance tomography (MRT) or the color-coded doppler ultrasound method, this way creating the possibility to control and if necessary to correct the insertion process.

The above-described procedures are again illustrated in detail in FIG. 13, whereby the sensors, respectively the ultrasound receivers are marked with the reference numeral 27. The reference numeral 28 in FIG. 13 c) indicates the focal point onto which the externally guided light of the cutting laser 30 is focussed.

The respective dark areas shown in FIG. 13 indicate the guided light of the orientation laser 29, respectively the cutting laser 30. As can be seen from the embodiment examples of FIG. 13, the light of the orientation laser 29, respectively of the cutting laser 30 can be guided in the same or in different elements.

In FIG. 14, which basically corresponds to FIG. 4, an additional adapter 31 is provided for an external ultrasound device or an orientation laser.

I claim:

1. A device for access to a vein of a patient by penetration of skin of the patient, comprising:
   a mounting member provided with means for affixing the mounting member to skin of the patient in proximity to a vein to be accessed;
   connection means on said mounting member for connection of at least one unit selected from a syringe unit and an infusion unit to said mounting member;
   a cannula on the mounting member having an end adapted to penetrate into said vein and communicating with said connection means for interconnecting said unit with said vein;
   a light-conductive cutting element on said mounting member having a sleeve portion surrounding said cannula at least at said end and juxtaposed with the skin of the patient for directing a high-energy light beam of a wavelength in the visible range or a range adjacent the visible range onto the skin to pierce the skin and penetrate the vein, the cannula being insertable through a tubular cut made by said high-energy light beam into the skin and said vein;
   a source of high-energy light of said wavelength in the visible range or said range adjacent the visible range connected to said light conductive element, and measuring means on said mounting member for positioning said cutting element by photoelectric plethysmography to pierce said vein.

2. The device defined in claim 1, further comprising at least one light-conductive rod connecting said source with said sleeve.

3. The device defined in claim 1 wherein said sleeve is formed on a light conductive rod connected to said source.

4. The device defined in claim 1 wherein said source of high-energy light is a laser.

5. The device defined in claim 1 wherein said source is a source of monochromatic light.

6. The device defined in claim 5 wherein said source is connected with said sleeve by two diametrically opposite rods.

7. The device defined in claim 1, further comprising a light conductor extending through said cannula and connected to said detector.

8. The device defined in claim 4, further comprising an optical splitter for passing measuring light to the skin and light from the skin to the detector.

9. The device defined in claim 1 wherein said means for affixing the mounting member to the skin of the patient is an adhesive foil on said mounting member.

10. The device defined in claim 9, further comprising an attachment part of spherical segmental shape having a dome and a flat bottom portion across said dome and located between said foil and said mounting member, said mounting member being embedded in said attachment part, said foil being provided on said flat bottom portion of said attachment part.

11. The device defined in claim 9, further comprising an anaesthetic-impregnated cushion on said foil in a region in which said cannula is adapted to penetrate the skin.

12. The device defined in claim 9, further comprising a protective foil on said adhesive foil on a surface thereof adapted to be pressed against the skin, said protective foil being strippable from said adhesive foil.

13. The device defined in claim 1 wherein said sleeve is connected to said source through said connection means.

14. The device defined in claim 13, further comprising a connector having optical fibers operatively connected to said sleeve at said connection means.

15. The device defined in claim 14 wherein said cannula is longitudinally shiftable in said mounting means.

16. The device defined in claim 15, further comprising a setting element for displacing said cannula in a region at which said connector is connected to said light-conducting element.

17. The device defined in claim 1 wherein said measuring means includes a measuring light source for directing measuring light onto the skin, and a detector for receiving transmitted or reflected light from the skin.

18. The device defined in claim 17 wherein said measuring light source is a laser.

19. The device defined in claim 17 wherein said source of high-energy light and said measuring light source is a single laser of adjustable output power and wavelength.

20. The device defined in claim 17, further comprising measuring circuitry connected to said detector for at least one of analog, digital and fuzzy logic evaluation of signals from said detector.

21. The device defined in claim 20 wherein said measuring circuitry has means for generating a signal indicating positioning of said cutting element for piercing said vein.

* * * * *